United States Patent [19]

Karges

[11] 3,985,620

[45] Oct. 12, 1976

[54] SUBSTRATE FOR DETERMINING PROTEINASE

[75] Inventor: Hermann Erich Karges, Marbach near Marburg an der Lahn, Germany

[73] Assignee: Behringwerke Aktiengesellschaft, Marburg an der Lahn, Germany

[22] Filed: Dec. 19, 1974

[21] Appl. No.: 534,166

[30] Foreign Application Priority Data

Dec. 21, 1973 Germany............................ 2363854

[52] U.S. Cl............................ 195/103.5 R; 195/99; 195/101
[51] Int. Cl.². ........................................... C12K 1/04
[58] Field of Search.................. 195/103.5 R, 63, 68

[56] References Cited
UNITED STATES PATENTS 3,751,262  8/1973  Ku et al. .............................. 426/218
3,775,253  11/1973  Dieter et al. .......................... 195/63

OTHER PUBLICATIONS

H. Rinderknecht et al., "A New Ultrasensitive Method for the Determination of Proteolytic Activity" Clin. Chim. Acta 21, pp. 197–203 (1968).

Primary Examiner—A. Louis Monacell
Assistant Examiner—C. A. Fan
Attorney, Agent, or Firm—Curtis, Morris & Safford

[57] ABSTRACT

Substrate for determining proteinases wherein a substrate protein is bound by a covalent bond in fine distribution in or on the surface of a solid carrier and dyed with a reactive dyestuff, its manufacture and its use.

15 Claims, 1 Drawing Figure

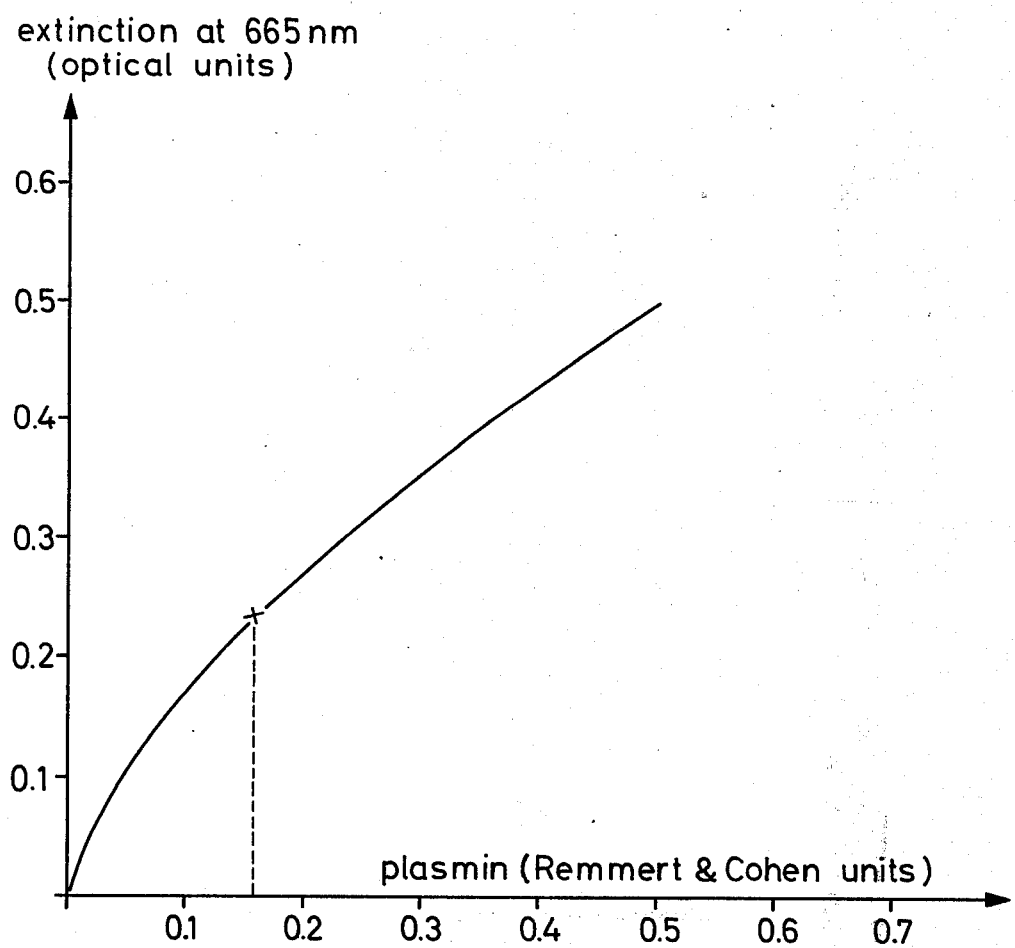

SUBSTRATE FOR DETERMINING PROTEINASE

The present invention provides a substrate for determining proteinase.

More particularly, it relates to a solid substrate for determining proteinase which is especially suitable for use in colored solutions, for example in hemoglobin or chlorophyll containing media.

For determining proteinase, a great number of processes is described in the literature, which processes can virtually be subdivided into two groups, the first one comprising those in which highmolecular weight protein bodies are split and the second one those based on the hydrolysis of low molecular weight substances, such as esters and amides. In the second group the cleavage products often have an altered light absorption as compared with the intact substrate. The altered light absorption in the absorption peak of the cleavage products is often used as a measure for enzyme activity. Usually, it is assumed that the action of proteinase on high molecular weight substrates is the same as on low molecular weight material. However, this is not true in complex systems which contain inhibitors in addition to enzymes, for example in the blood. Using high molecular weight substrates, such as hemoglobin, gelatin or casein, the proteolytic action of the solution can be determined correctly, however, with the drawback that the substrates must be separated from the degradation product by precipitation after the incubation time with the enzyme and must frequently be ascertained by means of sensitive, chemical reaction. Those activity measurements are highly erroneous and considerable errors are introduced when the measurements require optical reading and proteinase containing solution shows an absorption of its own interfering with the field of measurement.

Attempts have been made to dye high molecular weight substrates with reactive dyestuffs and to determine the hydrolytic proteinase action of the amount of dyestuff split off by photometry [cf. H. Rinderknecht et al., Clin. Chim. Acta 21, 197–203 (1968)]. The drawback of this method is that the particle size of the dyed hide powder has a considerable influence on its sensitivity.

Now, a highly sensitive solid substrate for determining proteinases has been found wherein a substrate protein is finely dispersed in or on the surface of a solid carrier bound thereto by a covalent bond and is dyed with a reactive dyestuff. Due to its fine dispersion, the high molecular weight substrate is very accessible to the proteinases to be determined and the cleavage of the substrate leads to the release of the dyestuff coupled thereto depending on the enzyme activity.

Suitable substrate proteins of the invention are all proteins capable of being split by proteinases, especially hemoglobin, casein, fibrinogen or collagen and the conversion or modification products thereof, such as heat fibrin, α-casein, gelatin, furthermore, cross-linked hydrolysis products of these compounds, for example cross-linked polypeptides from degraded gelatin, which are prepared according to German Patent No. 1,118,792 and are available in commerce under the name of Haemaccel (registered trade mark of Behringwerke AG).

Suitable carriers for these substrates are, above all copolymers of an active monomer, i.e., a monomer that contains active groups, like the carboxylic acid anhydride or the isocyanate group, and an inactive monomer free of such groups, for example an ether. Suitable active monomers are especially maleic acid or crotonic acid anhydride or allyl isothiocyanate. Suitable inactive monomers are, for example, propylene, acrylamide or butadiene.

The copolymers may be of active an inactive monomers in any desired quantitative ratio, so monomer units of the active monomer of from 0.01 to 99.99 mol % can be contained in the polymer. The copolymer of maleic acid anhydride and acrylamide will advantageously contain less than about 6 mole % of maleic acid anhydride, the copolymer of maleic acid anhydride and butadiene less than about 90 mol % of maleic acid anhydride, while the copolymer of maleic acid anhydride and propylene advantageously consists of about 50 % of maleic acid anhydride and 50 % of propylene. If an especially high proportion of active groups is desired, a homopolymer of the active monomer, for example of the maleic acid anhydride, can be used as carrier for the substrate protein, too.

The carrier must then be reacted with the substrate protein so that the active groups of both reactants form covalent bonds. The type of the reaction and the covalent bonds formed thereby naturally depend on the character of the active groups reacting. For example, in corresponding addition or condensation reactions, peptide, urea, thiourea, ester, acetal or ether bonds can be formed. Should excess reactive groups which have not reacted with the substrate proteins remain in the carrier material, they can be removed, if desired, by suitable low molecular weight reactants, for example acid anhydride groups by an amine, such as hexamethylene diamine.

Further bonds with an inert carrier (for example polyacryl amide, polyamide) according to the invention can be formed by introducing reactive groups, such as isothiocyanate reactive double bonds, diazonium groups, azo groups or reactive halogens into the substrate proteins, which then react with the carrier according to the usual chemical methods. If the carrier itself is provided with reactive groups, the substrate can be bound thereto in the same manner as described above.

The reactive dyestuff is chosen with respect to the preferred field of use of the substrate. To measure the proteinase in the blood or in media containing hemoglobin, especially extracts of organs, the dyestuffs preferably used have an absorption peak with wave lengths of >600 nm because in this range an influence exercised by the self-absorption of the hemoglobin is minimum. An especially suitable dyestuff for this purpose is Remazol[R] (registered trade mark of Hoechst AG) turquoise blue B (C.I.: Reactive blue 77). Further dyestuffs suitable for dyeing substrates are, for example Procion[R] (registered trade mark of ICI) turquoise blue H 7 G (C.I. Reactive blue 3), Remazol[R] black RL (.C.I. Reactive black 31), Cibacron[R] (registered trade mark of Ciba AG) turquoise blue G-E (C.I. Reactive blue 7), Cibacron[R] turquoise blue FGF-P (C.I. 74460, Reactive blue 15).

In the case of plant extracts containing chlorophyll, dyestuffs can be chosen that have at least one absorption peak not interfering with chlorophyll, for example Remazol[R] brilliant red FB (C.I. reactive red 104) and Remazol[R] brilliant red BB(C.I. Reactive red 21).

The substrate bound on or in the carrier in covalent manner is dyed under pH and temperature conditions that are recommended by the dyestuff manufacturers. After the reaction of the dyestuff with the substrate, the excess dyestuff is washed out in the corresponding absorption peak while controlling the extinction. A solid substrate prepared according to this process for determining the proteinase is more sensitive by a factor of 5 to 100 than are the high molecular weight substrates dyed according to the state of the art.

The invention also relates to the use of the substrate and agents containing that substrate for measuring proteinase activities.

After incubation of the solutions containing proteinase with the dyed substrate bound to the carrier, incubation which can be carried out at 0° – 80° C depending on the temperature sensitivity of the proteinase to be determined, preferably at 20° – 40° C, the readily centrifugeable and filtrable carrier is separated and the dyestuff set free is measured in its absorption peak. The extinction so obtained shows a linear dependence on the proteinase activity to be measured in a wide field. Extinction outside the linear field can be avoided by diluting the enzyme solution. Due to the covalent bond of the substrate protein to the carrier and of the dyestuff to the substrate protein, the substrate reamins stable in a large pH range (pH 2 – 12) during the time required for the test. While substrates which are adsorbed on the carrier are easily separated by modification of the salt medium or by the presence of proteins, for example albumin, the substrate according to the invention allows the use of different buffer systems, which may be selected according to their best capacity to measure the proteinase.

The substrates of the invention can be used for determining proteinases which is made with a sensitivity not yet observed with known substrates, for example trypsin, chymotrypsin, collagenase, bromelain, ficin or pronase. The manufacture of the substrate of the invention and its use for determining proteinases, especially in the blood, in tissue and plant extracts is described in the examples that follow:

The following Examples illustrate the invention:

EXAMPLE 1

400 mg of a pulverulent polymer of maleic acid anhydride and propylene in the molar ratio 1 : 1 were made into a paste with 10 ml of 0.2 M phosphate buffer pH 7.5 and diluted to 20 ml in a cooling bath of an ice and water mixture with the same phosphate buffer to. A solution of 120 mg of human fibrinogen in 12 ml of 0.15 M NaCl-solution was added. To destroy excess anhydride groups, 8 ml of hexamethylene diamine were added. The mixture was stirred over night, decanted and the gel was washed three times with 40 ml of 0.9 % sodium chloride solution.

After washing out the unlinked fibrinogen, the gel was suspended in 75 ml of a trisodium phosphate buffer that contained 720 mg of $Na_3PO_4 \cdot 12 H_2O$ and stirred for 3 hours at 40° C in a water bath by adding 360 mg of Remazol[R] turquoise blue B (C.I. Reactive blue 77). The gel was precipitated by centrifuging, stirred with 400 ml of a 0.9 % sodium chloride solution at 80° C and again centrifuged. That washing operation for eliminating the excess dyestuff having no covalent bond was repeated 10 times, the first two washings being carried out with a sodium chloride solution that contained 0.2 ml of a 2 N sodium chloride solution per 100 ml. The next 5 washings were effected with sodium chloride solution without additives, the 8th washing was performed with sodium chloride solution containing 0.5 g of bovine albumin per 100 ml. The last two washing solutions did not contain any additives. Centrifuging followed and the yield was determined. 1.2 g of moist substrate were obtained. To prepare a substrate composition for determining plasmin, the precipitate was suspended in 3.6 ml of a 0.1 M sodium citrate buffer of pH 7.4 The proteinase substrate so obtained can directly be used for determining the activity.

The same good results were obtained when the substrate was lyophilized for storage and was resuspended in the corresponding amount of water immediately before use.

EXAMPLE 2

To 150 mg of bovin fibrinogen in 20 ml of 0.15 M NaCl, 5 ml 0.1 M phosphate buffer, (pH 7.6) were added and then, 15 mg of maleic acid anhydride were added portionwise and the whole was allowed to react for half an hour at room temperature. The maleoyl fibrinogen so obtained was copolymerized according to L- Ornstein [cf. Annal. N.Y. Acad. Sci. 121, 321, 1964)]with acrylamide. The polymer mixture consisted of the solutions A and C proposed by Ornstein and an ammonium peroxide disulfate solution having the following composition:

Solution A:
  48 ml of 1 N HCl
  36.3 g of trishydroxymethyl aminomethane
  0.46 ml of TEMED = tetraethylmethyl-ethylene diamine to 100 ml of distilled water, Solution C:
  (according to Ornstein with modifications)
  30 g of acryl amide
  1.5 g of methylene bisacryl amide
  to 100 ml of distilled water ammoniumperoxide disulfate:
  1 % solution in distilled water.

The copolymerization of 25 ml of the maleoyl-fibrinogen solution obtained as described above was initiated by adding 5 ml of solution A, 6.25 ml of solution C and 1.25 ml of ammonium peroxide disulfate solution and completed at room temperature during an hour's standing. The gel was covered with 80 ml of 0.9 % sodium chloride solution and comminuted with a laboratory homogenizer. The product was centrifuged and stirred with the same amount of 0.9 % sodium chloride solution, again centrifuged and the residue suspended in 24 ml of a trisodium phosphate buffer which contained 0.9 g of trisodium phosphate. 0.45 g of Remazol[R] turquoise blue B (C.I. Reactive blue 77). The mixture was stirred at 40° C for 3 hours. The excess dyestuff was washed as described in Example 1 in detail, 240 ml of a 0.9 % sodium chloride solution and, optionally, the additives named in Example 1 being added for each washing operation.

EXAMPLE 3

3 g of horse hemoglobin were dissolved in 300 ml of 0.1 M phosphate buffer, pH 7.4, to which 900 mg of pulverulent maleic acid anhydride were added. The mixture was stirred for half an hour. The maleoyl hemoglobin so obtained was copolymerized as described in Example 2 with acrylamide to yield a 5 % acrylamide gel. For the polymerization the solutions according to Ornstein were used as has been described in Example 2 in the following quantitative ratios: To 300 ml of the maleoyl hemoglobin solution 60 ml of the solution A according to Ornstein, 75 ml of the solution C and 15 ml of the 1 % ammonium peroxide disulfate solution were added. After an hour's standing at room temperature the gel was covered with 900 ml of a 0.9 % sodium chloride solution and comminuted with a laboratory homogenizer. The copolymer was centrifuged and shortly stirred with the same amount of a 0.9 % sodium chloride solution, then centrifuged and the residue was suspended in 450 ml of a trisodium phosphate buffer which contained 10.8 g of $Na_3PO_4 \cdot 12\ H_2O$ and stirred at 25° C with 5.4 g of Remazol$^{(R)}$ turquoise blue B (C.I. Reactive blue 77) for 18 hours. The excess dyestuff was washed as described in Example 1, 4.5 l of the washing solution being used in the order mentioned.

EXAMPLE 4

1 g of fibrinogen was dissolved in 100 ml of 0.2 M phosphate buffer, pH 7.4, and reacted with 10.4 mg (10 $\mu$l) of crotonic acid anhydride. The crotonyl derivative of the fibrinogen formed during the standing of the reaction mixture was copolymerized in the manner described in Example 2 with acrylamide at pH 8.5 to give a 4 % gel. To this effect, 100 ml of the crotonyl fibrinogen solution were reacted with the polymer solutions according to Ornstein indicated in Example 2, 25 ml of solution A, 20 ml of solution C and 5 ml of ammonium peroxide disulfate being added. After 1 hour the gel was covered with 300 ml of a 0.9 % sodium chloride solution, comminuted with a laboratory homogenizer, centrifuged, washed once with sodium chloride solution, again centrifuged and suspended in 150 ml of a trisodium phosphate buffer which contained 1 g of trisodium phosphate and then reacted with 0.5 g of Remazol$^{(R)}$ turquoise blue B (C.I. Reactive blue 77) at 40° C. The excess dyestuff was washed out as has been described in Example 1 using 1.5 l of the washing solution for each operation.

EXAMPLE 5

10 g of gelatin were dissolved in 0.1 M phosphate buffer, (pH 8.5) at 60° C and reacted at about 30° C with 56.5 $\mu$l (58.5 mg) of allyl isothiocyanate, which yielded the allyl isothio urea derivative. According to Example 2, this derivative was copolymerized with acrylamide at pH 8.5 to give a 4 % gel. To this effect, 100 ml of a 10 % allyl isothio urea gelatin solution were reacted as in Example 2 with the solutions according to Ornstein, 25 ml of solution A, 20 ml of solution C and 5 ml of ammonium peroxide disulfate solution being used in this case. After an hour, the gel was covered with 300 ml of 0.9 % sodium chloride solution, comminuted with a laboratory homogenizer, centrifuged, washed once with a sodiumm chloride solution, again centrifuged and suspended in 150 ml of a trisodium phosphate buffer which contained 9.2 g of trisodium phosphate and reacted with 4.6 g of Remazol$^{(R)}$ turquoise blue B (C.I. Reactive blue 77) at 40° C. The excess dyestuff was washed out according to Example 1 using 1.5 l of the washing solution for each washing operation.

EXAMPLE 6

100 ml of Haemaccel$^{(R)}$ having a protein content of 10% were mixed with 100 ml of 0.1 M phosphate buffer at pH 8.5 and reacted with 56.5 g of maleic acid anhydride at 30° C. According to Example 2, the maleoylated Haemaccel was copolymerized with acrylamide at pH 8.5 to give a 4 % gel. To this effect 200 ml of the maleoyl-Haemacel solution were reacted with the polymerization solutions according to Ornstein as described in Example 2, 50 ml of solution A, 40 ml of solution C and 10 ml of ammonium peroxide disulfate solution being added. After an hour the gel was covered with 600 ml of 0.9 % sodium chloride solution, comminuted with a laboratory homogenizer, centrifuged, washed once with sodium chloride solution, again centrifuged and suspended in 300 ml of a trisodium phosphate buffer which contained 9.2 g of trisodium phosphate and reacted with 4.6 g of Remazol$^{(R)}$ turquoise blue B (C.I. Reactive blue 77) at 40° C. The excess dyestuff was washed out according to Example 1 using 3 l of the washing solution for each washing operation.

EXAMPLE 7

1 g of casein was dissolved in 0.1 M citrate buffer (pH 7.4) to give a 10 % solution. At room temperature, 0.2 ml of poly-ethylene glycol-$\alpha,\omega$ di-(sulfophenyl-4-isothiocyanate) having a molecular weight of 1000 to 6000 was added and stirred until the solution solidified. After an hour the gel was comminuted. After washing out the unbound protein with 2 × 50 ml of a 0.1 M citrate buffer at pH 7.4, the gel was centrifuged and suspended in 50 ml of a trisodium phosphate buffer which contained 1 g of trisodium phosphate and reacted with 0.5 g of Remazol$^{(R)}$ brilliant red FB (C.I. Reactive red 104) and maintained at 40° C for 3 hours. The excess dyestuff was washed out according to Example 1 using 1 l of washing solution for each washing operation.

EXAMPLE 8

600 mg of $\alpha$-casein were dissolved in 0.05 M tris buffer (pH 7.5) which contained 0.09 M NaCl to give a 3 % solution, which was heated to 80° C for 1 hour. After cooling to 30° C 0.15 ml of polyethylene glycol-$\alpha$, $\omega$ di-(sulfophenyl-4-isothiocyanate) of a molecular weight of 500 to 1000 was added and the mixture was stirred until it solidified. After 1 hour the gel was comminuted and the unbound protein was washed out with 2 × 100 ml of a 0.1 M citrate buffer of pH 7.4, centrifuged and suspended in 20 ml of a trisodium phosphate buffer which contained 600 mg of trisodium phosphate. To this suspension 300 mg of Procion$^{(R)}$ turquoise blue H 7 G (C.I. Reactive blue 3) were added, maintained at 40° C for half an hour and heated to 80° C for another 30 minutes. After cooling, the excess dyestuff was washed out according to Example 1 using 200 ml of the washing solution for each washing operation.

TEST 1

To 50 mg of a lyophilized substrate suspended in physiological sodium chloride according to Example 2, 2 ml of distilled water and 2 ml of 0.1 M citrate buffer of pH 7.4 were pipetted and the mixture was allowed to stand for 5 minutes at room temperature. A homogeneous suspension was prepared using a glass rod and this suspension was incubated at 37° C in a water bath for 5 minutes. 2 ml of citrated blood of a patient under fibrinolysis therapy were added to the substrate immediately after being taken out of the arm vein and the mixture was thoroughly stirred. Incubation followed at 37° C for 15 minutes while shaking three times. The degradation was stopped after 15 minutes by adding 1 ml of a dilute solution of the Kunitz Trypsin inhibitors with 500 KIE/ml. After centrifuging the substrate for 10 minutes at 3000 rpm in a laboratory centrifuger, the clear excess was siphoned off and measured at 665 nm in a spectrophotometer. With the aid of a calibration curve, the plasmin activity could be read off. For example, for a patient under fibrinolysis therapy for 10 minutes, a ΔE 665 nm of 0.235 OE was found. A calibration curve drawn by means of defined amounts of plasmin, shown in FIG. 1, displayed a plasmin activity for this moment of 0.16 units according to Remmert & Cohen.

By modifying the test conditions, for example the following enzymes could be determined:

| Enzyme | Substrate*) | Buffer | pH | Incubation temperature | Incubation period |
| --- | --- | --- | --- | --- | --- |
| Trypsin | Haemaccel | 0.05 M Tris | 8.0 | 37°C | 15 min. |
| Chymotrypsin | Gelatin | 0.05 M phosphate | 7.5 | 37°C | 15 min. |
| Collagenase | Collagen | 0.1 M citrate | 7.4 | 37°C | 30 min. |
| Bromelain | Casein | 0.1 M acetate | 4.0 | 40°C | 30 min. |
| Ficin | Hemoglobin | 0.05 M Tris | 8.5 | 40°C | 20 min. |
| Pronase | Casein | 0.06 M Borate | 9.0 | 40°C | 10 min. |

*Any desired carrier and dyestuff can be chosen for the invention.

TEST 2

This test is for comparing the sensitivity of the substrate of the invention with a known commercial product manufactured from the denatured collagen of cow hide to which a blue dyestuff is bound, at the absorption peak of each. The enzyme used is Trypsin (Serva, 2 × crystallized). The degradation was effected in 0.05 M Tris at pH 7.8 at 37° C for 15 minutes and stopped with a proteinase inhibitor. The volume of the reaction mixture was 6 ml.

| Amount of Trypsin ng | Substrate I (commercial product) ΔE 595 nm | Substrate II (substrate of the invention) ΔE 665 nm |
| --- | --- | --- |
| 0 | 0.00 | 0.00 |
| 10 | not tested | 0.045 |
| 50 | 0.001 | 0.260 |
| 100 | 0.004 | 0.485 |
| 10.000 | 0.670 | not tested |

The figures in the comparison test show that the substrate of the invention is much more sensitive than the substrate used so far in industry.

What is claimed is:

1. A substrate for determining proteinases which comprises a substrate protein bound by covalent bonding to a solid polymer carrier and dyed with a reactive dyestuff.

2. A substrate as in claim 1 wherein the substrate protein is selected from the group consisting of hemoglobin, casein, fibrinogen, collagen, and modification products of these proteins.

3. A substrate as in claim 1 wherein said polymer carrier is selected from the group consisting of homopolymers of an active monomer and copolymers of an active and an inactive monomer.

4. A substrate as in claim 3 wherein said active monomer is selected from the group consisting of maleic acid anhydride, crotonic acid anhydride, and allyl isothiocyanate.

5. A substrate as in claim 3 wherein said inactive monomer is selected from the group consisting of propylene, acrylamide, and butadiene.

6. A substrate as in claim 3 wherein said polymer carrier is a copolymer of maleic acid anhydride and acrylamide containing up to 6 mol percent of maleic acid anhydride.

7. A substrate as in claim 3 wherein said polymer carrier is a copolymer of maleic acid anhydride and butadiene containing up to about 90 mol percent of maleic acid anhydride.

8. A substrate as in claim 3 wherein said polymer carrier is a copolymer of equal parts of maleic acid anhydride and propylene.

9. A substrate as in claim 1 wherein said polymer carrier is a homopolymer of maleic acid anhydride.

10. A substrate as in claim 1 wherein said reactive dyestuff is one having its absorption peak at a wave length greater than 600 nm.

11. A process for the manufacture of a substrate for determining proteinases, which comprises reacting a carrier of a copolymer of an active and an inactive monomer with a substrate protein to covalently bond the active groups of the carrier with those of the substrate protein and dyeing the reaction product with a reactive dyestuff.

12. A process for the manufacture of a substrate for determining proteinases which comprises reacting a carrier free of active groups with a substrate protein in the presence of a substance yielding active groups and dyeing the reaction product with a reactive dyestuff.

13. A process for the manufacture of a substrate for determining proteinases which comprises introducing reactive groups into a substrate protein, then copolymerizing the protein with an inactive monomer, and dyeing the reaction product with a reactive dyestuff.

14. A process for the manufacture of a substrate for determining proteinases which comprises cross-linking a soluble polymer having reactive groups with a substrate protein and dyeing the reaction product with a reactive dyestuff.

15. A process for determining proteinases which comprises contacting a substrate as in claim 1 with an aqueous solution of a proteinase, separating the liquid phase, and measuring the extinction of the separated liquid phase.

* * * * *